United States Patent
Rodatz et al.

(10) Patent No.: US 8,037,671 B2
(45) Date of Patent: Oct. 18, 2011

(54) METHOD AND DEVICE FOR THE CALIBRATION OF AN EXHAUST GAS PROBE, AND METHOD AND DEVICE FOR THE OPERATION OF AN INTERNAL COMBUSTION ENGINE

(75) Inventors: Paul Rodatz, Landshut (DE); Gerd Rösel, Regensburg (DE)

(73) Assignee: Continental Automotive GmbH, Hannover (DE)

( * ) Notice: Subject to any disclaimer, the term of this patent is extended or adjusted under 35 U.S.C. 154(b) by 732 days.

(21) Appl. No.: 12/097,162
(22) PCT Filed: Nov. 13, 2006
(86) PCT No.: PCT/EP2006/068383
§ 371 (c)(1),
(2), (4) Date: Jun. 12, 2008
(87) PCT Pub. No.: WO2007/068541
PCT Pub. Date: Jun. 21, 2007

(65) Prior Publication Data
US 2008/0307852 A1    Dec. 18, 2008

(30) Foreign Application Priority Data
Dec. 14, 2005   (DE) .......................... 10 2005 059 794

(51) Int. Cl.
*F01N 3/00* (2006.01)
(52) U.S. Cl. ................ 60/276; 60/274; 60/285; 60/286; 73/23.32; 73/114.72; 701/103; 701/109; 701/114
(58) Field of Classification Search .................... 60/277, 60/285, 296, 299; 73/23.32, 114.72, 114.73; 123/679, 981, 964; 701/103, 109, 114
See application file for complete search history.

(56) References Cited

U.S. PATENT DOCUMENTS 6,439,038 B1 *   8/2002   Rosel et al. ................ 73/114.73
(Continued)

FOREIGN PATENT DOCUMENTS

| DE | 10161901 | 12/2001 |
| DE | 102005004441 | 1/2005 |
| WO | 2004/085819 | 10/2004 |
| WO | 2006/053802 | 5/2006 |

OTHER PUBLICATIONS

Laurell et al.; "A Metal Substrate eith Integrated Oxygen Sensor; Functionality and Influence on Air/Fuel Ratio Control"; SAE International; pp. 8, 2003.

*Primary Examiner* — Thomas Denion
*Assistant Examiner* — Patrick Maines
(74) *Attorney, Agent, or Firm* — King & Spalding L.L.P.

(57) ABSTRACT

A plateau phase of a test signal of an exhaust gas probe located in a catalytic converter is detected following a jump from a preset rich air/fuel ratio in a combustion chamber of one cylinder to a preset lean air/fuel ratio, the plateau phase being obtained following the jump, and the duration is determined as a storage period. A plateau phase of the test signal, which is obtained following a jump from a preset lean air/fuel ratio to a preset rich air/fuel ratio, is detected following the jump, and the duration of the plateau phase is determined as an evacuation period. An allocation rule for assigning the test signal to a detected air/fuel ratio is adjusted according to the storage period and the evacuation period. To calibrate the exhaust gas probe, the allocation rule is adapted according to a plateau value of the test signal during the plateau phase.

7 Claims, 6 Drawing Sheets

U.S. PATENT DOCUMENTS

| | | | |
|---|---|---|---|
| 7,673,443 B2 * | 3/2010 | Rodatz et al. | 60/274 |
| 2004/0050378 A1 * | 3/2004 | Yamashita | 123/694 |
| 2007/0000482 A1 | 1/2007 | Tamura et al. | 123/687 |
| 2007/0295000 A1 * | 12/2007 | Rodatz et al. | 60/274 |
| 2008/0120017 A1 | 5/2008 | Rodatz et al. | 701/108 |
| 2009/0100922 A1 * | 4/2009 | Korbel et al. | 73/114.72 |

\* cited by examiner

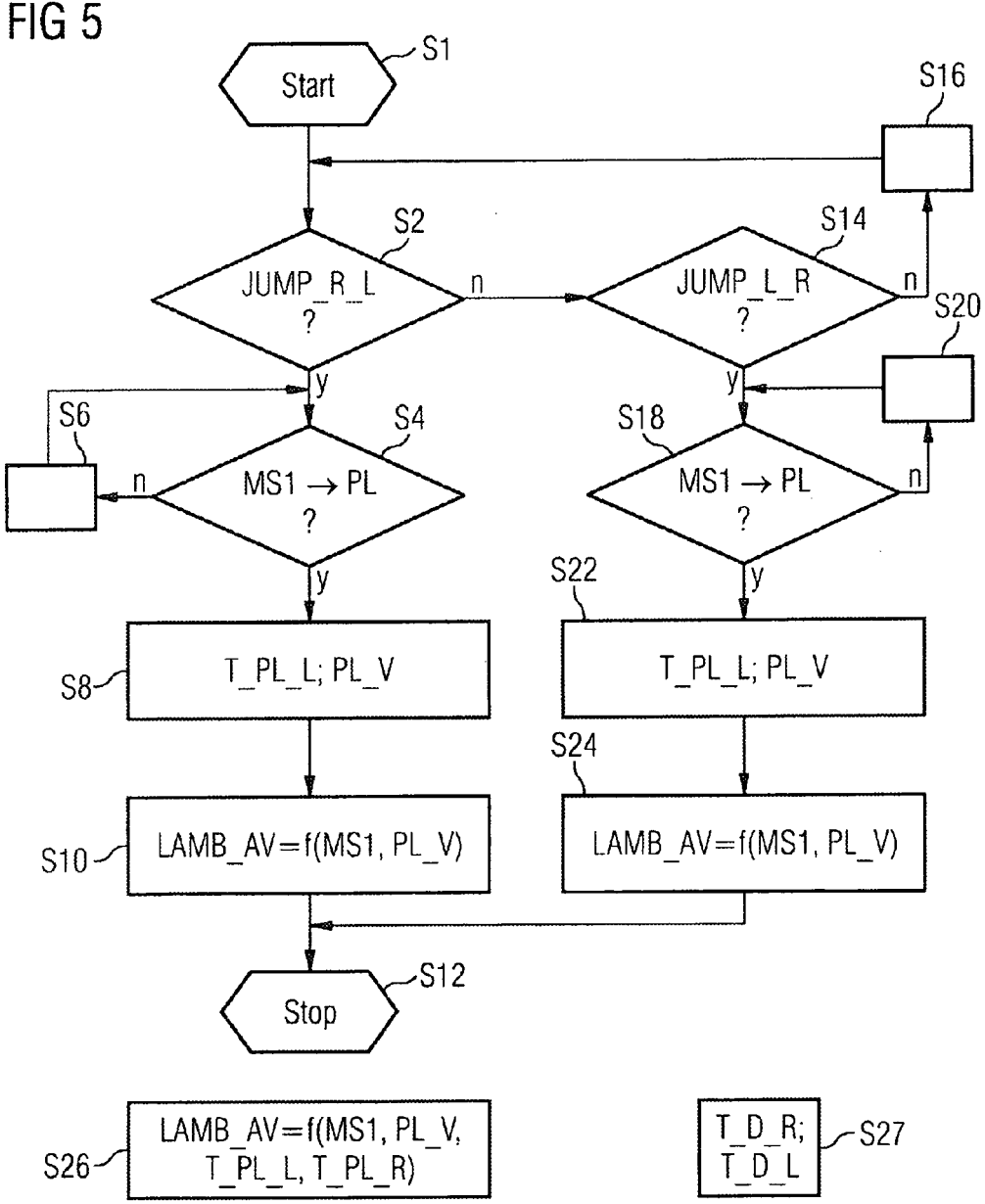

FIG 6

S28
$$K = f(T\_PL\_L, T\_PL\_R, D\_LAMB\_SP\_R \mid D\_LAMB\_SP\_L)$$

$$K = 1((T\_PL\_L/T\_PL\_R) - (T\_PL\_L/T\_PL\_R)*D\_LAMB\_SP\_R - D\_LAMB\_SP\_R) \quad (F1)$$

$$K = 1((T\_PL\_R/T\_PL\_L) - (T\_PL\_R/T\_PL\_L)*D\_LAMB\_SP\_L - D\_LAMB\_SP\_L) \quad (F2)$$

S30
$$LAMB\_AV = f(MS1, PL\_V, K)$$

FIG 7

S32
$$LAM\_FAC\_MEAN = f(LAM\_FAC\_FB)$$

S34
$$D\_LAM\_FAC\_R = f(LAM\_FAC, LAM\_FAC\_MEAN)$$

S36
$$D\_LAM\_FAC\_L = f(LAM\_FAC, LAM\_FAC\_MEAN)$$

S38
$$K = f(T\_PL\_L, T\_PL\_R, D\_LAMB\_FAC\_R \mid D\_LAMB\_FAC\_L)$$

$$K = 1((T\_PL\_L/T\_PL\_R) - (T\_PL\_L/T\_PL\_R)*D\_LAMB\_FAC\_R - D\_LAMB\_FAC\_R) \quad (F3)$$

$$K = 1((T\_PL\_R/T\_PL\_L) - (T\_PL\_R/T\_PL\_L)*D\_LAMB\_FAC\_L - D\_LAMB\_FAC\_L) \quad (F4)$$

S40
$$T\_D\_R = f(K)$$
$$T\_D\_L = f(K)$$

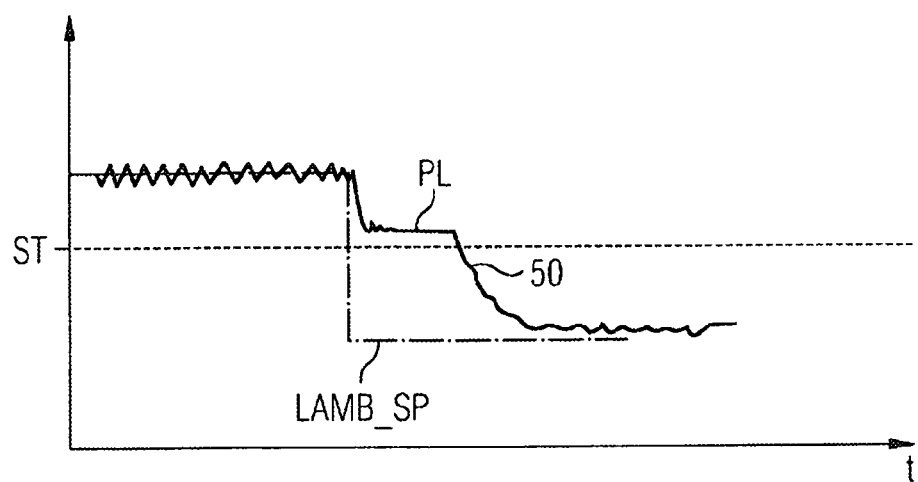
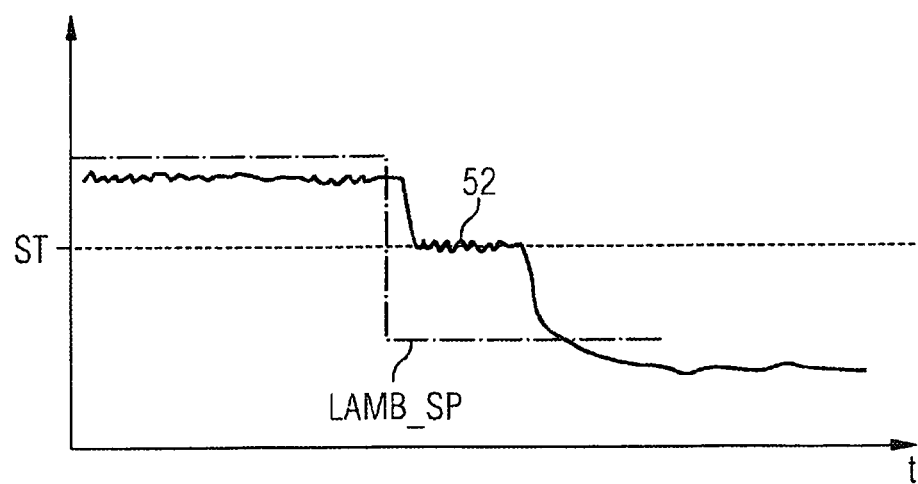

METHOD AND DEVICE FOR THE CALIBRATION OF AN EXHAUST GAS PROBE, AND METHOD AND DEVICE FOR THE OPERATION OF AN INTERNAL COMBUSTION ENGINE

CROSS-REFERENCE TO RELATED APPLICATIONS

This application is a U.S. national stage application of International Application No. PCT/EP2006/068383 filed Nov. 13, 2006, which designates the United States of America, and claims priority to German application number 10 2005 059 794.7 filed Dec. 14, 2005, the contents of which are hereby incorporated by reference in their entirety.

TECHNICAL FIELD

The invention relates to a method and a device for calibrating an exhaust gas probe arranged in an exhaust catalytic converter in an exhaust system of an internal combustion engine. The invention also relates to a method and a device for operating the internal combustion engine.

BACKGROUND

Ever stricter statutory regulations regarding permissible pollutant emissions from motor vehicles which have internal combustion engines make it necessary to keep the pollutant emissions as low as possible during operation of the internal combustion engine. This can be achieved, on the one hand, in that the pollutant emissions which arise during combustion of the fuel/air mixture in the respective cylinder of the internal combustion engine are reduced. On the other hand, exhaust treatment systems which convert the pollutant emissions which are produced during combustion of the fuel/air mixture in the respective cylinder into harmless substances are used in internal combustion engines. For this purpose, catalytic converters which convert carbon monoxide, hydrocarbons and nitrogen oxides into harmless substances are used. Both targeted influencing of the production of the pollutant emissions during combustion and the conversion of the pollutant components with a high level of efficiency by an exhaust catalytic converter require a very precisely adjusted air/fuel ratio in the respective cylinder.

The SAE International publication "A Metal Substrate with Integrated Oxygen Sensor; Functionality and Influence on Air/Fuel Ratio Control", Mats Laurell et al., SAE 2003-01-0818, describes a device for an internal combustion engine with a catalytic converter in the exhaust system. A linear lambda sensor is arranged in the exhaust system upstream from the exhaust catalytic converter. Also arranged in the exhaust catalytic converter are a first and a second binary lambda probe. The binary lambda probe is used for trimming the probe signal from the linear lambda sensor. The measured signal from the linear lambda sensor which is thus trimmed is the control variable of the lambda controller.

From the textbook "Handbuch Verbrennungsmotor", edited by Richard von Basshuysen, Fred Schäfer, $2^{nd}$ edition, Vieweg & Sohn Verlagsgesellschaft mbH, June 2002, pages 559-561, a linear lambda control system is known which has a linear lambda probe arranged upstream of an exhaust catalytic converter, and a binary lambda probe which is arranged downstream of the exhaust catalytic converter. A target lambda value is filtered by a filter which takes account of the delays and the sensor behavior. The thus filtered lambda target value is the control variable of a $PII^2D$-Lambda controller whose manipulated variable is an injection quantity correction.

Also known from the textbook "Handbuch Verbrennungsmotor", edited by Richard von Basshuysen, Fred Schäfer, $2^{nd}$ edition, Vieweg & Sohn Verlagsgesellschaft mbH, June 2002, pages 559-561, is a binary lambda control system which has a binary lambda probe arranged upstream of the exhaust catalytic converter. The binary lambda control system also comprises a PI controller wherein the P and I components are stored in engine characteristic maps as engine speed and load. With the binary lambda control, excitation of the catalyst, also denoted as lambda oscillation, is implicitly produced by two-step control. The amplitude of the lambda oscillation is set to about three percent.

SUMMARY

A method for calibrating an exhaust gas probe which is simple and precise and a method and a device for operating an internal combustion engine which are simple and precise can be provided. According to an embodiment, a method for calibrating an exhaust gas probe arranged in an exhaust catalytic converter of an internal combustion engine in an exhaust system and whose measured signal represents an air/fuel ratio in the combustion chamber of the respective cylinder, may comprise the steps of: —following a jump from a preset rich air/fuel ratio in the combustion chamber of the respective cylinder to a preset lean air/fuel ratio, a plateau phase which occurs thereafter in the measured signal is detected, and/or following a jump from the preset lean air/fuel ratio in the combustion chamber of the respective cylinder to the preset rich air/fuel mixture, a plateau phase which occurs thereafter in the measured signal is detected, and—depending on the plateau value of the measured signal, an allocation rule for assigning the measured signal to a detected air/fuel ratio is adjusted.

According to another embodiment, a method for operating an internal combustion engine, with—at least one cylinder with a combustion chamber, —an injection valve which is provided for dosing in the fuel, and—an exhaust system in which an exhaust gas probe is arranged in an exhaust catalytic converter, the measured signal from said probe representing an air/fuel ratio in the combustion chamber of the respective cylinder, wherein a linear lambda control system is provided, the method may comprise the steps of: —following a jump from a preset rich air/fuel ratio in the combustion chamber of the respective cylinder to a preset lean air/fuel ratio, a plateau phase which occurs thereafter in the measured signal is detected and the duration of the plateau phase is determined as a storage period, —following a jump from a preset lean air/fuel ratio in the combustion chamber of the respective cylinder to a preset rich air/fuel ratio, a plateau phase which occurs thereafter in the measured signal is detected and the duration of the plateau phase is determined as an evacuation period and—depending on the storage period and the evacuation period, an allocation rule for assigning the measured signal to a detected air/fuel ratio is adjusted.

According to a further embodiment, —following a jump from a preset rich air/fuel ratio in the combustion chamber of the respective cylinder to a preset lean air/fuel ratio, a plateau phase which occurs thereafter in the measured signal is detected, and/or following a jump from the preset lean air/fuel ratio in the combustion chamber of the respective cylinder to the preset rich air/fuel ratio, a plateau phase which occurs thereafter in the measured signal is detected, and—depending on the plateau value of the measured signal, the allocation rule for assigning the measured signal to the detected air/fuel ratio is adjusted.

According to another embodiment, a method for operating an internal combustion engine with at least one cylinder with a combustion chamber, an injection valve which is provided for dosing in the fuel, an exhaust system in which an exhaust gas probe is arranged in an exhaust catalytic converter, the measured signal from said probe representing an air/fuel ratio in the combustion chamber of the respective cylinder, wherein a binary lambda control system is provided, the method may comprise the steps of: —following a jump from a preset rich air/fuel ratio in the combustion chamber of the respective cylinder to a preset lean air/fuel ratio, a plateau phase which occurs thereafter in the measured signal is detected and the duration of the plateau phase is determined as a storage period, —following a jump from a preset lean air/fuel ratio in the combustion chamber of the respective cylinder to a preset rich air/fuel ratio, a plateau phase which occurs thereafter in the measured signal is detected and the duration of the plateau phase is determined as an evacuation period and —depending on the storage period and the evacuation period, a control parameter of the binary lambda control system is adjusted.

According to a further embodiment, the control parameter may be a proportional jump delay duration. According to a further embodiment, the proportional jump delay duration may be a rich proportional jump delay duration.

According to yet another embodiment, a device for calibrating an exhaust gas probe arranged in an exhaust catalytic converter of an internal combustion engine in an exhaust system and whose measured signal represents an air/fuel ratio in the combustion chamber of the respective cylinder, may be operable: —following a jump from a preset rich air/fuel ratio in the combustion chamber of the respective cylinder to a preset lean air/fuel mixture, to detect a plateau phase which occurs thereafter in the measured signal, and/or following a jump from the preset lean air/fuel mixture in the combustion chamber of the respective cylinder to the preset rich air/fuel mixture, to detect a plateau phase which occurs thereafter in the measured signal, and—to adjust an allocation rule for assigning the measured signal to a detected air/fuel ratio, depending on the plateau value of the measured signal.

According to yet another embodiment, a device for operating an internal combustion engine may comprise—at least one cylinder comprising a combustion chamber, —an injection valve which is provided for dosing in the fuel, and—an exhaust system in which an exhaust gas probe is arranged in an exhaust catalytic converter, the measured signal from said probe representing an air/fuel ratio in the combustion chamber of the respective cylinder, wherein a linear lambda control system is provided, wherein the device is operable: —following a jump from a preset rich air/fuel ratio in the combustion chamber of the respective cylinder to a preset lean air/fuel ratio, to detect a plateau phase which occurs thereafter in the measured signal and to determine the duration of the plateau phase as a storage period, —following a jump from a preset lean air/fuel ratio in the combustion chamber of the respective cylinder to a preset rich air/fuel ratio, to detect a plateau phase which occurs thereafter in the measured signal and to determine the duration of the plateau phase as an evacuation period and—to adjust an allocation rule for assigning the measured signal to a detected air/fuel ratio, depending on the storage period and the evacuation period.

According to yet another embodiment, a device for operating an internal combustion engine may comprise at least one cylinder comprising a combustion chamber, an injection valve which is provided for dosing in the fuel, and an exhaust system in which an exhaust gas probe is arranged in an exhaust catalytic converter, the measured signal from said probe representing an air/fuel ratio in the combustion chamber of the respective cylinder, wherein a binary lambda control system is provided, wherein the device is operable: —following a jump from a preset rich air/fuel ratio in the combustion chamber of the respective cylinder to a preset lean air/fuel ratio, to detect a plateau phase which occurs thereafter in the measured signal and to determine the duration of the plateau phase as a storage period, —following a jump from a preset lean air/fuel mixture in the combustion chamber of the respective cylinder to a preset rich air/fuel ratio, to detect a plateau phase which occurs thereafter in the measured signal and to determine the duration of the plateau phase as an evacuation period and—to adjust a control parameter of the binary lambda control system, depending on the storage period and the evacuation period.

BRIEF DESCRIPTION OF THE DRAWINGS

Exemplary embodiments of the invention are described in more detail below with reference to the schematic drawings, in which:

FIG. 5 shows a flow chart for the operation of the internal combustion engine, FIGS. 6 and 7 show further detail from the flow chart of FIG. 5, and FIGS. 8 and 9 show signal curves.

DETAILED DESCRIPTION

Figure 1:
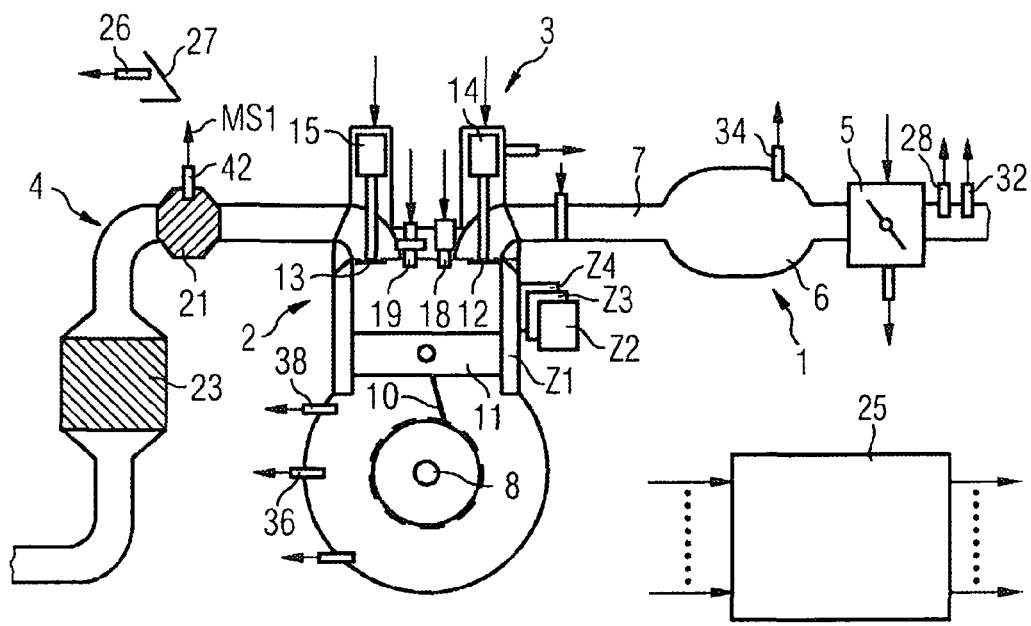
FIG. 1 shows an internal combustion engine.

According to a first aspect, in a method and a corresponding device for calibrating an exhaust gas probe which is arranged in an exhaust catalytic converter in an exhaust system of an internal combustion engine and whose measured signal represents an air/fuel ratio in the combustion chamber of the respective cylinder, following a jump from a preset rich air/fuel ratio in the combustion chamber of the respective cylinder to a preset lean air/fuel ratio, a plateau phase which occurs thereafter in the measured signal is detected. The presetting of the respective air/fuel ratio also comprises, in particular, corresponding control of a respective injection valve for dosing fuel into the respective combustion chamber.

Alternatively or additionally, following a jump from the preset lean air/fuel ratio in the combustion chamber of the respective cylinder to the preset rich air/fuel mixture, a plateau phase which occurs thereafter in the measured signal is detected. Depending on the plateau value of the measured signal, an allocation rule for assigning the measured signal to a detected air/fuel ratio is adjusted.

In this regard, the surprising discovery that with the exhaust gas probe arranged in the exhaust catalytic converter, when a jump occurs from a preset rich air/fuel mixture to a preset lean air/fuel mixture, the excess oxygen which is then present is initially stored in the upstream region of the exhaust catalytic converter and therefore neither oxygen nor fuel components flow past in the region of the exhaust gas probe and that therefore the plateau value of the measured signal represents a stoichiometric air/fuel ratio in the combustion chamber of the cylinder is made use of. Therefore through the simple detection of the plateau phase, which is easily possible, by means of allocation of the associated plateau value, easy and precise calibration of the exhaust gas probe is possible. It is therefore possible to dispense with a second exhaust gas probe which otherwise would be usual for such purposes, arranged downstream of the exhaust catalytic converter.

A similar principle applies for a jump from the preset lean air/fuel ratio to the rich air/fuel ratio, wherein by means of evacuation—or clearance—the oxygen bound into the catalyser material can react with the excess fuel component and therefore no oxygen residue and no fuel residue are found in the region of the exhaust gas probe, until the catalyst material upstream of the exhaust gas probe is cleared of oxygen.

According to a second aspect, in a method and a corresponding device for operating the internal combustion engine with at least one cylinder comprising a combustion chamber, an injection valve which is provided for dosing in the fuel, and an exhaust system in which an exhaust gas probe is arranged in an exhaust catalytic converter, the measured signal from said probe representing an air/fuel ratio in the combustion chamber of the respective cylinder, a linear lambda control system is provided. Following a jump from a preset rich air/fuel ratio in the combustion chamber of the respective cylinder to a preset lean air/fuel ratio, a plateau phase which occurs thereafter in the measured signal is detected and the duration of the plateau phase is determined as a storage period. Following a jump from a preset lean air/fuel ratio in the combustion chamber of the respective cylinder to a preset rich air/fuel ratio, a plateau phase which occurs thereafter in the measured signal is detected and the duration of the plateau phase is determined as the evacuation period. Depending on the storage period and the evacuation period, an allocation rule for assigning the measured signal to a detected air/fuel ratio is adjusted. In this case, also, the discovery that with the exhaust gas probe arranged in the exhaust catalytic converter, when a jump occurs from a preset rich air/fuel mixture to a preset lean air/fuel mixture, the excess oxygen which then arises is initially stored in the upstream region of the exhaust catalytic converter and therefore neither oxygen nor fuel components flow past in the region of the exhaust gas probe and that therefore the plateau value of the measured signal represents a stoichiometric air/fuel ratio in the combustion chamber of the cylinder is made use of. A similar principle applies also for a jump from a preset lean air/fuel ratio to the rich air/fuel ratio, wherein the evacuation of the oxygen bound into the catalyst material can react with the excess fuel component and therefore no oxygen and no fuel component are found in the region of the exhaust gas probe, until the catalyst material upstream of the exhaust gas probe has been evacuated.

The storage period is representative of the period required to completely store oxygen in the catalyst material upstream of the exhaust gas probe until said material can no longer absorb any further oxygen. The evacuation period is representative of the period needed in the event of the rich air/fuel ratio until all oxygen components, which were originally bound into the catalyst material upstream of the exhaust gas probe, are evacuated due to the flow of fuel components past it.

Since, during the storage period, the same oxygen mass is bound into the catalyst material as is cleared out of it during the evacuation period, the difference between the storage period and the evacuation period represents air/fuel ratios which deviate unequally from the stoichiometric air/fuel ratio during the storage period and during the evacuation period for instance. This is attributable, in connection with a linear lambda control system with a predetermined air/fuel ratio in the respective combustion chamber which, when averaged over time, is stoichiometric, to incorrect conversion of the measured signal from the exhaust gas probe to the detected air/fuel ratio and can therefore be corrected by adjusting the detected air/fuel ratio depending on the storage period and the evacuation period with regard to the allocation rule for assigning the measured signal.

In this regard, it is advantageous if additionally the allocation rule for assigning the measured signal to the detected air/fuel ratio is adjusted, according to the first aspect, depending on the plateau value of the measured signal. By this means, a more precise operation of the internal combustion engine can be ensured.

According to a third aspect, in a method and a corresponding device for operating the internal combustion engine with at least one cylinder comprising a combustion chamber, an injection valve which is provided for dosing in fuel, and an exhaust system in which an exhaust gas probe is arranged in an exhaust catalytic converter, the measured signal from said probe representing an air/fuel ratio in the combustion chamber of the cylinder, a binary lambda control system is provided.

Following a jump from a preset rich air/fuel ratio in the combustion chamber of the respective cylinder to a preset lean air/fuel ratio, a plateau phase which occurs thereafter in the measured signal is detected and the duration of the plateau phase is determined as a storage period. Following a jump from a preset lean air/fuel ratio in the combustion chamber of the respective cylinder to a preset rich air/fuel ratio, a plateau phase which occurs thereafter in the measured signal is detected and the duration of the plateau phase is determined as an evacuation period. Depending on the storage period and the evacuation period, a control parameter of the binary lambda control system is adjusted. By this means, also, the characteristics of the plateau phase can advantageously be used for precise setting of the actual air/fuel ratio in the respective combustion chamber for a binary lambda control system.

According to an advantageous embodiment of the third aspect, the control parameter can be a proportional jump delay duration and by this means, a desired stoichiometric air/fuel ratio in the respective combustion chamber of the cylinder can be set particularly easily as a mean value.

Furthermore, it may be advantageous in this regard if the proportional jump delay duration is a rich-proportional jump delay duration. By this means, the actual air/fuel ratio can be set particularly precisely in the respective combustion chamber to the stoichiometric air/fuel ratio. In this regard, use is made of the recognition that normally the inaccuracy of the exhaust gas probe in the enriched region of the air/fuel ratio is greater.

Elements which have the same design or function are the same in all the figures and are identified with the same reference characters.

An internal combustion engine (FIG. 1) comprises an intake system 1, an engine block 2, a cylinder head 3 and an exhaust system 4. The intake system 1 preferably comprises a throttle valve 5, a collecting pipe 6 and an inlet manifold 7, which leads to a cylinder Z1 via an inlet port into the engine block 2. The engine block 2 also comprises a crankshaft 8 which is coupled via a piston rod 10 to the piston 11 of the cylinder Z1.

The cylinder head 3 also comprises a valve mechanism with a gas inlet valve 12 and a gas outlet valve 13.

The cylinder head 3 also comprises an injection valve 18 and a spark plug 19. Alternatively, the injection valve 18 can also be arranged in the inlet manifold 7.

Arranged in the exhaust system is an exhaust catalytic converter which is configured as a three-way catalytic converter 21. Preferably also arranged in the exhaust system is a further exhaust catalytic converter which is configured as a NOx catalytic converter 23.

A control device 25 is provided to which sensors which detect various measuring variables and determine the value of the measuring variable are allocated. Depending on at least one of the measuring variables, the control device 25 determines manipulated variables which are then converted into one or more control signals for controlling the actuators by means of suitable actuating drives. The control device 25 can also be identified as a device for controlling the internal combustion engine.

The sensors are a pedal position sensor 26 which detects the position of an accelerator pedal 27, an airflow sensor 28 which detects an airflow upstream of the throttle valve 5, a first temperature sensor 32, which detects an intake air temperature, an inlet manifold pressure sensor 34 which detects an inlet manifold pressure in the collecting pipe 6, a crankshaft angle sensor 36 which detects a crankshaft angle, to which an engine speed is then assigned.

An exhaust gas probe 42 is also provided, which is arranged in the three-way catalytic converter 21 and which detects a residual oxygen content of the exhaust gas and whose measured signal MS1 is characteristic of the air/fuel ratio in the combustion chamber of the cylinder Z1 and upstream of the first exhaust gas probe before the oxidation of the fuel, designated in the following text as the air-fuel ratio in the cylinders Z1-Z4. The first exhaust gas probe 42 is arranged in the three-way catalytic converter 21 such that part of the catalytic converter volume is situated upstream of the exhaust gas probe 42.

The exhaust gas probe 42 can be a linear lambda probe or a binary lambda probe.

Depending on the embodiment, an arbitrary lesser quantity of the sensors named, or additional sensors, may be present.

The actuators are, for example, the throttle valve 5, the gas inlet and outlet valves 12, 13, the injection valve 18 or the spark plug 19.

Apart from the cylinder Z1, preferably other cylinders Z2 to Z4 are also provided, to which other corresponding actuators and/or sensors are also allocated.

Figure 2:
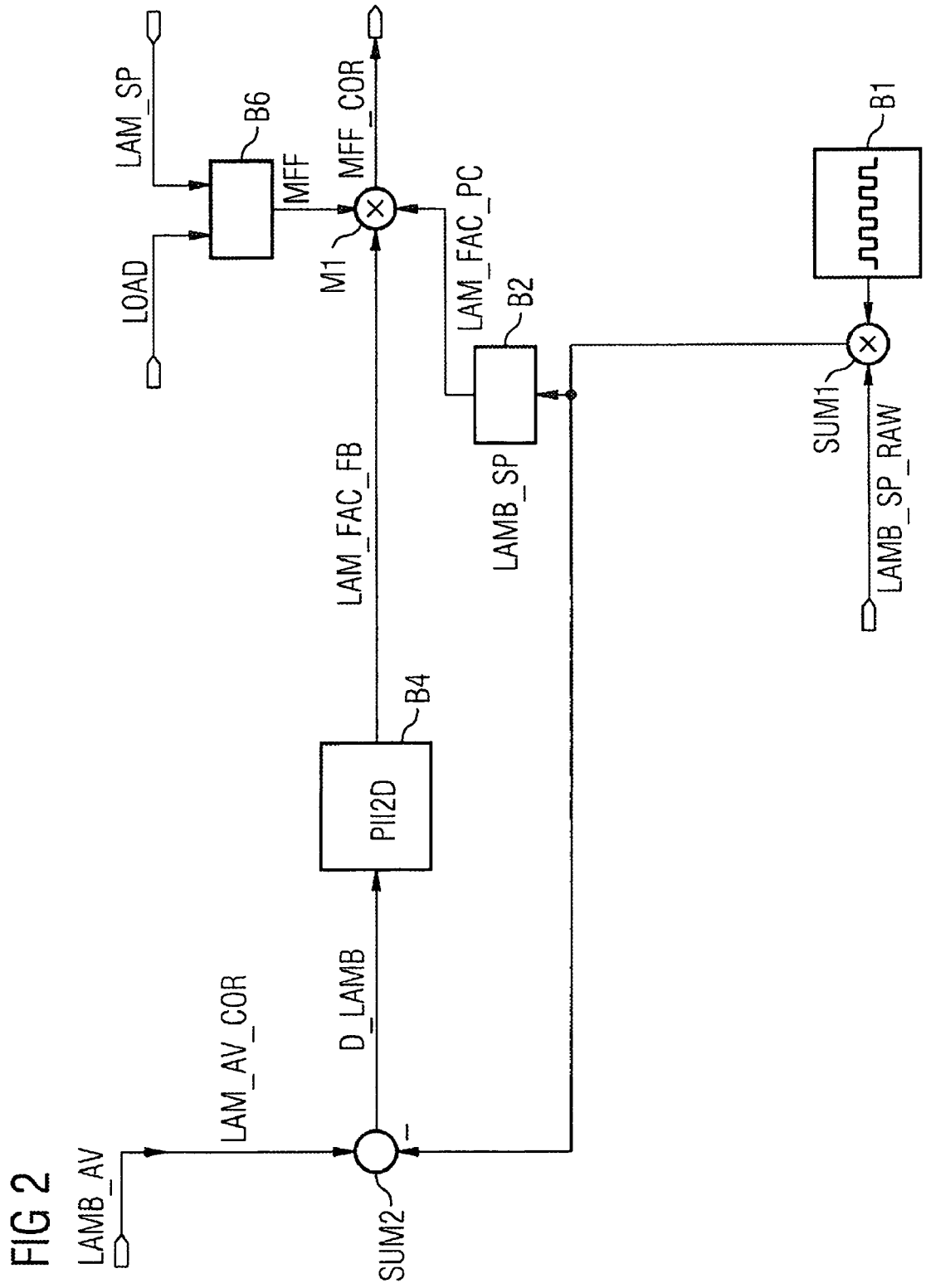
FIG. 2 shows a block diagram of part of the control device of the internal combustion engine in a first embodiment.

A block diagram of part of the control device 25 according to a first embodiment is shown in FIG. 2. In a particularly special embodiment, a preset raw air/fuel ratio LAMB_SP_RAW can be stipulated in advance. However, it is preferable, for example, depending on the current operating mode of the internal combustion engine, such as a homogenous or layered operation and/or dependent on operating variables of the internal combustion engine. In particular, the pre-determined raw air/fuel ratio LAMB_SP_RAW can be specified as approximately the stoichiometric air/fuel ratio. Operating variables include measuring variables and variables derived therefrom.

A forced excitation is determined in a block B1 and added in the first summing point SUM1 to the pre-determined raw air/fuel ratio LAMB_SP_RAW. The forced excitation is a rectangular signal. The output variable of the summing point is then a pre-determined air/fuel ratio LAMB_SP in the combustion chambers of the cylinders Z1 to Z4. The pre-determined air/fuel ratio LAMB_SP is fed to a block B2 which comprises a precontrol system and a lambda precontrol factor LAMB_FAC_PC which depends on the pre-determined air/fuel ratio LAMB_SP.

In a second summing point SUM2, depending on the pre-determined air/fuel ratio LAMB_SP and the determined air/fuel ratio LAMB_AV, by calculating the difference between them, a control difference D_LAMB is found which is the input variable to a block B4. The block B4 contains a linear lambda controller, which is preferably a $PII^2D$ controller. The manipulated variable of the linear lambda controller of the block B4 is a lambda control factor LAM_FAC_FB. The determination of the detected air/fuel ratio LAMB_AV is described below in greater detail by reference to FIGS. 5 to 7.

The pre-determined air/fuel ratio LAMB_SP can also be subjected to filtration before calculation of the difference in the summing point S2.

A block B6 is also provided in which, depending on a load LOAD, which can be, for example, an airflow, a fuel mass MFF to be dosed in is determined. In the multiplication point M1, a corrected fuel mass to be dosed in is determined by forming the product of the fuel mass MFF to be dosed in, the lambda precontrol factor LAM_FAC_PC and the lambda control factor LAM_FAC_FB. The injection valve 18 is then controlled accordingly for dosing in the corrected fuel mass MFF_COR to be dosed in.

Figure 3:
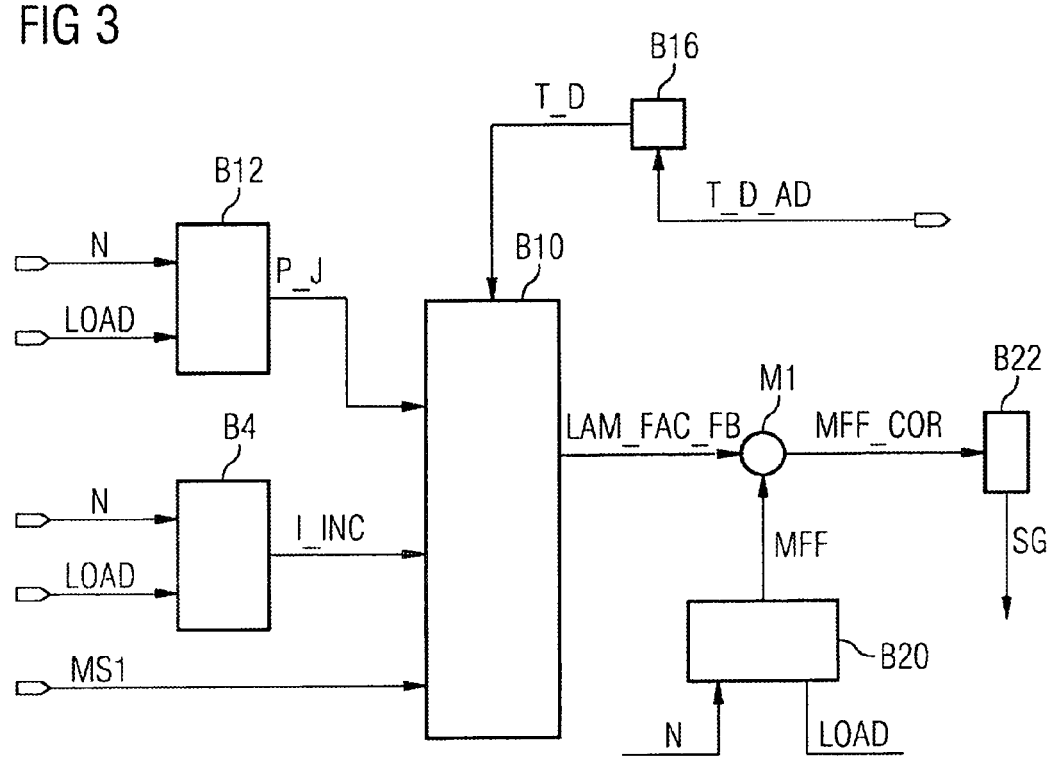
FIG. 3 shows another block diagram of part of the control device of the internal combustion engine according to a second embodiment.

Part of the control device 25 in a further embodiment with a binary lambda control system, will now be described in greater detail by reference to the block diagram of FIG. 3.

A block B10 comprises a binary lambda control system. The measured signal MS1 is fed to the binary lambda controller as the controlled variable. In this connection, the exhaust gas probe 42 is configured as binary lambda probe and the measured signal is therefore of an essentially binary nature, so that it assumes a lean value when the air/fuel ratio before the exhaust catalytic converter 21 is lean, and a rich value when it is rich. Only in a very small intermediate region, that is for example, with a precisely stoichiometric air/fuel ratio, does it assume intermediate values between the lean value and the rich value. Due to the binary nature of this type of measured signal MS1, the binary lambda controller is configured as a two-step controller. The binary lambda controller is preferably configured as a PI controller. A P-component is preferably fed as a proportional jump P_J to the block B10.

A block B12 is provided in which proportional jump P_J is determined depending on the rotary speed N and the load LOAD.

For this purpose, a characteristic map which can be safely stored is preferably provided.

An I-component of the binary lambda controller is preferably determined depending on an integral increment I_INC. The integral increment I_INC is preferably determined in a block B14, also depending on the rotary speed N and the load LOAD. For this purpose, a characteristic map can also be provided.

The load LOAD can be, for example, the airflow or even the inlet manifold pressure.

Furthermore, also fed to the block B10 as an input parameter is a delay period TD which is determined in a block B16 and preferably depending on a correction value K which will be described in greater detail by reference to FIG. 7. On the output side of the binary lambda controller, the lambda control factor LAM_FAC_FB is made available. A block B20 corresponds to the block B6. In a block B22, depending on the corrected fuel mass MFF_COR to be dosed in, a control signal SG for the respective injection valve 18 is generated.

Figure 4:
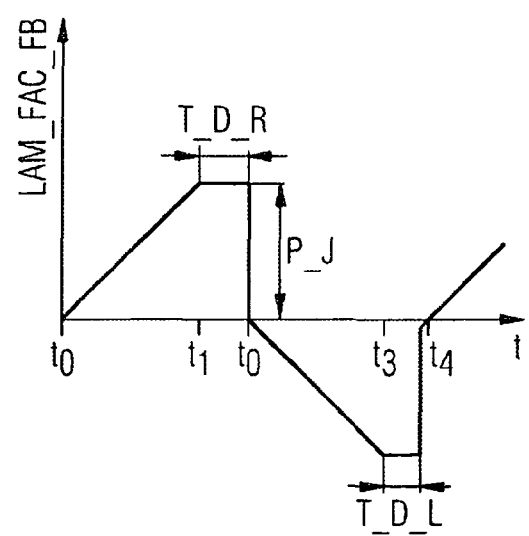
FIG. 4 shows the temporal course of a lambda control factor.

The functioning of the binary lambda controller will now be described in greater detail by reference to FIG. 4. At a time point t0, the lambda control factor LAM_FAC_FB has a neutral value, for example one, and is increased, starting at a time point to, depending on an integral increment I_INC, until a time point t1. For example, this occurs at a pre-determined time rate at which the current value of the lambda control factor LAM_FAC_FB and the integral increment I_INC is increased. The time point t1 is characterized in that the first measured signal MS1 jumps from its lean value to its rich value.

If it is found that the first measured signal MS1 has jumped from its lean value to its rich value, the lambda control factor LAM_FAC_FB is not further incremented by the integral increment I_INC, but its value is maintained for the delay period T_D and, indeed, in the event that the enriching has taken place, for the rich proportional jump delay duration T_D_R and, in the event that the ratio is made leaner, for the lean proportional jump delay duration T_D_L. When the delay period T_D expires, which is the case at a time point t2, the lambda control factor LAM_FAC_FB is reduced according to the proportional jump P_J. Following the jump of the lambda control factor LAM_FAC_FB, at the time point t2, the lambda control factor LAM_FAC_FB is reduced accordingly by the integral increment I_INC until the measured signal MS1 jumps from the rich value to the lean value, which is the case at the time point t3. Starting from time point t3, the lambda control factor LAM_FAC_FB remains at its value for the pre-determined lean proportional jump delay duration T_D_L before being increased again after expiry of the lean proportional jump delay duration T_D_L at a time point t4 by the proportional jump P_J and then beginning a new control period.

A program according to the flow diagram of FIG. 5 which runs during operation of the internal combustion engine and starts at step S will now be described in greater detail. The program is fundamentally suitable for use in conjunction with the first embodiment of the control device, but also in conjunction with the second embodiment of the control device 25 possibly when the steps have been adjusted.

The program can be restarted in step S1, for example, after respectively pre-determined crankshaft angles or time intervals or other pre-determined events. Preferably, variables are initialized in the first step S1.

In step S2, it is tested whether a rich-lean jump JUMP_R_L has taken place with respect to the preset air/fuel ratio in the combustion chamber of the respective cylinder Z1-Z4. In the case of the linear lambda control system as per FIG. 2, this takes place with corresponding stipulation of the pre-determined air/fuel ratio LAMB_SP, particularly in conjunction with the forced excitation. In the case of the binary lambda control system, this is done by the two-step control system when the lambda control factor LAMB_FAC_FB has made a proportional jump P_J to its value of the lambda control factor LAM_FAC_FB in the region of less than one.

If the condition of step S2 is fulfilled, then in step S4, it is checked whether the measured signal MS1 from the exhaust gas probe 42 is in a plateau phase PL. The plateau phase PL is characterized in that, subsequently to the jump from the preset rich air/fuel ratio in the combustion chamber to the preset lean air/fuel ratio, a change in the measured signal MS1 takes place before it assumes a nearly constant value. The plateau phase PL can therefore easily be detected by suitable evaluation of the values of the measured signal MS1 and, in particular, its changes. If the condition of step S4 is not fulfilled, then the program remains at step S6 for a pre-determined waiting period before processing is continued anew in step S4.

If, on the other hand, the condition of step S4 is fulfilled, then in step S8, the time span for which the plateau phase PL endures is temporarily stored as a storage period T_PL_L. Furthermore, the value of the measured signal MS1 during the plateau phase is temporarily stored as the plateau value PL_V. In alternative embodiments, either just the storage period T_PL_L or the plateau value PL_V is determined and temporarily stored.

In step S10, in the case of the linear lambda control system, the detected air/fuel ratio LAMB_AV in the combustion chamber of the respective cylinder Z1-Z4 is determined depending on the measured signal MS1 and the plateau value PL_V. This may take place, for example, in that the measured signal MS1 is corrected by the plateau value PL_V such that if the first measured signal MS1 assumes the plateau value PL_V, the stoichiometric air/fuel ratio is allocated to the detected air/fuel ratio LAMB_AV. The allocation between the measured signal MS1 or the corrected measured signal and the detected air/fuel ratio LAMB_AV is preferably carried out using a characteristic line which has previously been found from tests or simulations and is stored in the control device 25.

Alternatively, however, in step S10 detection of the air/fuel ratio LAMB_AV can take place by acquisition of starting values from the aforementioned characteristic line with respect to the first measured signal MS1 and the plateau value PL_V and then corresponding adjustment of the allocation rule to the detected air/fuel ratio LAMB. For example, the correction can be undertaken by means of a suitable offset value which is determined depending on the plateau value PL_V such that the detected air/fuel ratio LAMB_AV assumes the stoichiometric value if the measured signal MS1 assumes the plateau value PL_V. The program is then preferably ended at step S12.

If the condition of step S2 is not fulfilled, it is tested in step S4 whether a lean-rich jump JUMP_L_R has taken place when the air/fuel ratio in the combustion chamber of the respective cylinder was preset. This is the situation, for example, in the case of the linear lambda control system, on a change of the pre-determined air/fuel ratio LAMB_SP from the lean air/fuel ratio to the rich air/fuel ratio.

In the case of the binary lambda control system, this is the situation if the lambda control factor LAM_FAC_FB is adjusted by means of a positive proportional jump P_J correspondingly from a value of less than one to a value of greater than one.

If the condition of step S14 is not fulfilled, the program remains at step S16 for a pre-determined waiting period before the condition in step S2 is tested again.

If, however, the condition in step S14 is fulfilled in step S18, it is tested, similarly to step S4, whether the measured signal MS1 is in a plateau phase PL. If the condition of step S18 is not fulfilled, the program remains at step S20 for a pre-determined waiting period before processing is continued again at step S18.

If, however, the condition of step S18 is fulfilled in step S22, similarly to step S8, an evacuation period T_PL_R is determined depending on the duration within which the measured signal MS1 is situated in the plateau phase PL. Furthermore, the value of the measured signal MS1 during the plateau phase PL is allocated to the plateau value PL_V. Alternatively, either just the plateau value PL_V or the evacuation period T_PL_R can be determined during step S22.

Step S24 which follows, corresponds to step S10.

Determination of the detected air/fuel ratio LAMB_AV as per step S10 or step S24 preferably takes place accordingly when the program is not run according to FIG. 5 during operation of the internal combustion engine.

Alternatively to steps S10 and S24, a step S26 can be provided in which the detected air/fuel ratio LAMB_AV is determined depending on the measured signal MS1, the storage duration T_PL_L, the evacuation duration T_PL_R and optionally also depending on the plateau value PL_V. This will now be described in greater detail by reference to FIG. 6.

In step S28, a correction value K is determined depending on the storage duration T_PL_L, the evacuation duration T_PL_R and a rich-target deviation value D_LAMB_SP_R or a lean-target deviation value D_LAMB_SP_L. The rich-target deviation value D_LAMB_SP_R is preferably determined depending on the pre-determined air/fuel ratio LAMB_SP if this is preset as a sub-stoichiometric ratio in relation to the stoichiometric ratio. Correspondingly, the lean-target deviation value D_LAMB_SP_L is determined depending on the pre-determined air/fuel ratio LAMB_SP with a preset above-stoichiometric air/fuel ratio in the combustion chamber relative to the stoichiometric air/fuel ratio.

In an alternative embodiment, this can be carried out according to a relation F1 and, in another alternative, according to the relation F2. According to the relations F1 and F2, the recognition that the oxygen mass stored or evacuated, respectively, during the storage period T_PL_L or the evacuation period T_PL_R is identical is made use of and thus distortions of the characteristic line of the exhaust gas probe can be corrected.

Preferably, determination of the detected air/fuel ratio LAMB_AV takes place in step S30, depending on the measured signal MS1 of the exhaust gas probe 42 and the correction value K and optionally also depending on the plateau value PL_V. Thus, for example, depending on the correction value K, an offset value can be added to the measured signal MS1 or the offset value can be added to the starting value of the characteristic line determined by suitable application of the measured signal MS1 to a characteristic line.

The determination of the detected air/fuel ratio LAMB_AV can also take place independently of the processing of the program as per FIG. 5 during operation of the internal combustion engine, as per the procedure in step S30.

In addition, during determination of the detected air/fuel ratio LAMB_AV, the plateau value PL_V can also be taken into account in step S30 according to the procedure of step S10 or step S24.

In the case of the binary lambda control system, preferably instead of steps S10 and S24, a step S27 can be carried out if optionally, with successive runs of the program as per FIG. 5, both steps S8 and S22 have been processed. In step S27, a rich proportional jump delay duration T_D_R or a lean proportional jump delay duration T_D_L is determined.

This preferably takes place in accordance with the procedure of FIG. 7. In step S32, a mean value LAM_FAC_MEAN of the lambda control factor LAM_FAC_FB is determined by averaging over a period of the sequence of the lambda control factor LAM_FAC_FB according to FIG. 4, that is for example, from time point t0 to time point t4.

In step S34, a rich factor deviation value D_LAM_FAC_R is then determined by taking the difference between a maximum lambda control factor LAM_FAC_FB during the respective period and the mean value LAM_FAC_MEAN of the lambda control factor LAM_FAC_FB. In an alternative step S26, a lean factor deviation value D_LAM_FAC_L is determined depending on the difference between the mean value LAM_FAC_MEAN of the lambda control factor LAM_FAC_FB and a minimum lambda control factor during the respective period.

In step S38, the correction value K is then determined, and this is done depending on the storage period T_PL_L, the evacuation period T_PL_R and either the rich-target deviation value D_LAMB_SP_R or the lean-target deviation value D_LAMB_SP_L. Accordingly, preferably the correction value K is determined according to either a relation F3 or a relation F4.

Here, also, the principle which was described above in connection with step S28 for a linear lambda probe is applied accordingly to the binary lambda probe. Preferably, in step S40, the rich proportional jump delay duration T_D_R is adjusted accordingly if the correction value K was determined by means of formula F4 or the lean proportional jump delay duration T_D_L is adjusted depending on the correction value K if the correction value K was determined by means of the relation F3. The processing of step S40 then preferably takes place independently of whether the program has just been run according to FIG. 5 and it takes place during regular operation of the internal combustion engine.

The procedure according to steps S2 to S24 also represents a calibration process.

By taking account of the plateau value PL_V when adjusting the detected air/fuel ratio LAMB_AV to the stoichiometric value, if the measured signal MS1 assumes the plateau value PL_V, an exact balancing of the oxygen load of the catalyst volume of the exhaust catalytic converter 21 can be carried out upstream as well as downstream of the exhaust gas probe 42. By this means, an oxygen load-based forced excitation can be enabled. Furthermore, with oxygen balancing of this type, the sizes of errors can be determined and thereafter, corresponding adjustment of the fuel dosing can be compensated in the opposite direction.

In FIGS. 8 and 9, the results of determining the detected air/fuel ratio LAMB_AV are shown, for example, in the case of FIG. 8 without taking account of the plateau PL_V and, in the case of FIG. 9, taking account of the plateau value PL_V. The reference sign 50 denotes the shape of the detected air/fuel ratio LAMB_AV without corresponding correction depending on the plateau value PL_V or depending on the storage period T_PL_L and the evacuation period T_PL_R and 52 in FIG. 8 denotes the air/fuel ratio LAMB_AV detected, for example, according to the process in step S10 or in S24 or S26. ST denotes the actual stoichiometric air/fuel ratio.

The invention claimed is:

1. A method for operating an internal combustion engine, with
   at least one cylinder with a combustion chamber,
   an injection valve which is provided for dosing in the fuel, and
   an exhaust system in which an exhaust gas probe is arranged in an exhaust catalytic converter, the measured signal from said probe representing an air/fuel ratio in the combustion chamber of the respective cylinder, wherein a linear lambda control system is provided, the method comprising the steps of:
   following a jump from a preset rich air/fuel ratio in the combustion chamber of the respective cylinder to a preset lean air/fuel ratio, a plateau phase which occurs thereafter in the measured signal is detected and the duration of the plateau phase is determined as a storage period,
   following a jump from a preset lean air/fuel ratio in the combustion chamber of the respective cylinder to a preset rich air/fuel ratio, a plateau phase which occurs thereafter in the measured signal is detected and the duration of the plateau phase is determined as an evacuation period and depending on the storage period and the evacuation period, an allocation rule for assigning the measured signal to a detected air/fuel ratio is adjusted.

2. The method according to claim 1, wherein following a jump from a preset rich air/fuel ratio in the combustion chamber of the respective cylinder to a preset lean air/fuel ratio, a plateau phase which occurs thereafter in the measured signal is detected, and/or following a jump from the preset lean air/fuel ratio in the combustion chamber of the respective cylinder to the preset rich air/fuel ratio, a plateau phase which occurs thereafter in the measured signal is detected, and depending on the plateau value of the measured signal, the allocation rule for assigning the measured signal to the detected air/fuel ratio is adjusted.

3. A method for operating an internal combustion engine with at least one cylinder with a combustion chamber, an injection valve which is provided for dosing in the fuel, an exhaust system in which an exhaust gas probe is arranged in an exhaust catalytic converter, the measured signal from said probe representing an air/fuel ratio in the combustion chamber of the respective cylinder, wherein a binary lambda control system is provided, the method comprising the steps of:

following a jump from a preset rich air/fuel ratio in the combustion chamber of the respective cylinder to a preset lean air/fuel ratio, a plateau phase which occurs thereafter in the measured signal is detected and the duration of the plateau phase is determined as a storage period, following a jump from a preset lean air/fuel ratio in the combustion chamber of the respective cylinder to a preset rich air/fuel ratio, a plateau phase which occurs thereafter in the measured signal is detected and the duration of the plateau phase is determined as an evacuation period and depending on the storage period and the evacuation period, a control parameter of the binary lambda control system is adjusted.

4. The method according to claim 3, wherein the control parameter is a proportional jump delay duration.

5. The method according to claim 4, wherein the proportional jump delay duration is a rich proportional jump delay duration.

6. A device for operating an internal combustion engine comprising at least one cylinder comprising a combustion chamber an injection valve which is provided for dosing in the fuel, and an exhaust system in which an exhaust gas probe is arranged in an exhaust catalytic converter, the measured signal from said probe representing an air/fuel ratio in the combustion chamber of the respective cylinder, wherein a linear lambda control system is provided, wherein the device is operable:

following a jump from a preset rich air/fuel ratio in the combustion chamber of the respective cylinder to a preset lean air/fuel ratio, to detect a plateau phase which occurs thereafter in the measured signal and to determine the duration of the plateau phase as a storage period, following a jump from a preset lean air/fuel ratio in the combustion chamber of the respective cylinder to a preset rich air/fuel ratio, to detect a plateau phase which occurs thereafter in the measured signal and to determine the duration of the plateau phase as an evacuation period and to adjust an allocation rule for assigning the measured signal to a detected air/fuel ratio, depending on the storage period and the evacuation period.

7. A device for operating an internal combustion engine comprising at least one cylinder comprising a combustion chamber, an injection valve which is provided for dosing in the fuel, and an exhaust system in which an exhaust gas probe is arranged in an exhaust catalytic converter, the measured signal from said probe representing an air/fuel ratio in the combustion chamber of the respective cylinder, wherein a binary lambda control system is provided, wherein the device is operable:

following a jump from a preset rich air/fuel ratio in the combustion chamber of the respective cylinder to a preset lean air/fuel ratio, to detect a plateau phase which occurs thereafter in the measured signal and to determine the duration of the plateau phase as a storage period, following a jump from a preset lean air/fuel mixture in the combustion chamber of the respective cylinder to a preset rich air/fuel ratio, to detect a plateau phase which occurs thereafter in the measured signal and to determine the duration of the plateau phase as an evacuation period and to adjust a control parameter of the binary lambda control system, depending on the storage period and the evacuation period.

* * * * *